(12) United States Patent
Alijuri et al.

(10) Patent No.: US 9,533,116 B2
(45) Date of Patent: *Jan. 3, 2017

(54) METHODS AND DEVICES FOR PASSIVE RESIDUAL LUNG VOLUME REDUCTION AND FUNCTIONAL LUNG VOLUME EXPANSION

(71) Applicant: Pulmonx Corporation, Redwood City, CA (US)

(72) Inventors: Nikolai Alijuri, Hillsborough, CA (US); Rodney C. Perkins, Woodside, CA (US); Niyazi Beyhan, Santa Clara, CA (US)

(73) Assignee: PulmonX Corporation, Redwood City, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 13/938,025

(22) Filed: Jul. 9, 2013

(65) Prior Publication Data

US 2013/0296696 A1 Nov. 7, 2013

Related U.S. Application Data

(63) Continuation of application No. 12/820,547, filed on Jun. 22, 2010, now Pat. No. 8,496,006, which is a
(Continued)

(51) Int. Cl.
*A61M 16/04* (2006.01)
*A61M 16/20* (2006.01)
(Continued)

(52) U.S. Cl.
CPC ............ *A61M 16/0434* (2013.01); *A61B 5/08* (2013.01); *A61B 6/03* (2013.01); *A61B 17/1204* (2013.01);
(Continued)

(58) Field of Classification Search
CPC ............ A61M 2025/0078; A61M 2025/1052; A61M 2025/0076; A61M 25/10; A61M 25/0075; A61M 16/0434; A61B 17/1204
(Continued)

(56) References Cited

U.S. PATENT DOCUMENTS 3,322,126 A 5/1967 Rusch et al.
3,498,286 A 3/1970 Polanyi et al.
(Continued)

FOREIGN PATENT DOCUMENTS

EP 0791340 A1 8/1997
EP 0815803 A1 1/1998
(Continued)

OTHER PUBLICATIONS

Notice of allowance dated Feb. 2, 2015 for U.S. Appl. No. 12/407,709.
(Continued)

*Primary Examiner* — Rachel Young
*Assistant Examiner* — Douglas Sul
(74) *Attorney, Agent, or Firm* — Wilson Sonsini Goodrich & Rosati (57) ABSTRACT

The volume of a hyperinflated lung compartment is reduced by sealing a distal end of the catheter in an airway feeding the lung compartment. Air passes out of the lung compartment through a passage in the catheter while the patient exhales. A one-way flow element associated with the catheter prevents air from re-entering the lung compartment as the patient inhales. Over time, the pressure of regions surrounding the lung compartment cause it to collapse as the volume of air diminishes. Residual volume reduction effectively results in functional lung volume expansion. Option-
(Continued)

ally, the lung compartment may be sealed in order to permanently prevent air from re-entering the lung compartment.

5 Claims, 7 Drawing Sheets

Related U.S. Application Data continuation-in-part of application No. 11/685,008, filed on Mar. 12, 2007, now abandoned, and a continuation-in-part of application No. 11/296,951, filed on Dec. 7, 2005, now Pat. No. 7,883,471.

(60) Provisional application No. 60/645,711, filed on Jan. 20, 2005, provisional application No. 60/696,940, filed on Jul. 5, 2005, provisional application No. 60/699,289, filed on Jul. 13, 2005.

(51) Int. Cl.
| | |
|---|---|
| A61M 39/22 | (2006.01) |
| A61B 5/08 | (2006.01) |
| A61B 17/12 | (2006.01) |
| A61B 6/03 | (2006.01) |
| A61M 16/00 | (2006.01) |
| A61M 25/10 | (2013.01) |

(52) U.S. Cl.
CPC ... *A61B 17/12104* (2013.01); *A61B 17/12136* (2013.01); *A61M 16/208* (2013.01); *A61M 25/10* (2013.01); *A61M 2016/003* (2013.01); *A61M 2025/1052* (2013.01)

(58) Field of Classification Search
USPC ............ 128/200.24, 200.26, 207.14–207.16; 604/99.01, 99.03
See application file for complete search history.

(56) References Cited

U.S. PATENT DOCUMENTS

| | | | |
|---|---|---|---|
| 3,669,098 A | 6/1972 | Takahashi | |
| 3,677,262 A | 7/1972 | Zukowski | |
| 3,768,504 A | 10/1973 | Rentsch, Jr. | |
| 3,776,222 A | 12/1973 | Smiddy | |
| 3,794,026 A | 2/1974 | Jacobs | |
| 3,866,599 A | 2/1975 | Johnson | |
| 3,913,568 A | 10/1975 | Carpenter | |
| 4,041,936 A | 8/1977 | Carden | |
| 4,134,407 A | 1/1979 | Elam | |
| 4,147,169 A | 4/1979 | Taylor | |
| 4,327,720 A | 5/1982 | Bronson et al. | |
| 4,327,721 A | 5/1982 | Goldin et al. | |
| 4,382,442 A * | 5/1983 | Jones .............................. 604/28 |
| 4,453,545 A | 6/1984 | Inoue | |
| 4,468,216 A | 8/1984 | Muto | |
| 4,470,407 A | 9/1984 | Hussein | |
| 4,538,607 A | 9/1985 | Saul | |
| 4,567,882 A | 2/1986 | Heller | |
| 4,681,093 A | 7/1987 | Ono et al. | |
| 4,716,896 A | 1/1988 | Ackerman | |
| 4,742,819 A | 5/1988 | George | |
| 4,784,133 A | 11/1988 | Macklin | |
| 4,796,639 A | 1/1989 | Snow et al. | |
| 4,819,664 A | 4/1989 | Nazari | |
| 4,846,153 A | 7/1989 | Berci | |
| 4,850,371 A | 7/1989 | Broadhurst et al. | |
| 4,852,568 A | 8/1989 | Kensey | |
| 4,862,874 A | 9/1989 | Kellner | |
| 4,896,941 A | 1/1990 | Hayashi et al. | |
| 4,949,716 A | 8/1990 | Chenoweth | |
| 4,955,375 A | 9/1990 | Martinez | |
| 4,958,932 A | 9/1990 | Kegelman et al. | |
| 4,961,738 A | 10/1990 | Mackin | |
| 4,976,710 A | 12/1990 | Mackin | |
| 5,056,529 A | 10/1991 | de Groot | |
| 5,143,062 A | 9/1992 | Peckham | |
| 5,146,916 A | 9/1992 | Catalani | |
| 5,165,420 A | 11/1992 | Strickland | |
| 5,181,913 A | 1/1993 | Erlich | |
| 5,285,778 A | 2/1994 | Mackin | |
| 5,308,325 A | 5/1994 | Quinn et al. | |
| 5,309,903 A | 5/1994 | Long | |
| 5,329,940 A * | 7/1994 | Adair ........................ 128/200.26 |
| 5,331,947 A | 7/1994 | Shturman | |
| 5,361,753 A | 11/1994 | Pothmann et al. | |
| 5,447,165 A | 9/1995 | Gustafss | |
| 5,477,851 A | 12/1995 | Callaghan et al. | |
| 5,499,625 A | 3/1996 | Frass et al. | |
| 5,546,935 A | 8/1996 | Champeau | |
| 5,588,424 A | 12/1996 | Insler et al. | |
| 5,598,840 A | 2/1997 | Iund et al. | |
| 5,624,449 A | 4/1997 | Pham et al. | |
| 5,642,730 A | 7/1997 | Baran | |
| 5,645,519 A | 7/1997 | Lee et al. | |
| 5,653,231 A | 8/1997 | Bell | |
| 5,660,175 A | 8/1997 | Dayal | |
| 5,682,880 A | 11/1997 | Brain | |
| 5,707,352 A | 1/1998 | Sekins et al. | |
| 5,752,921 A | 5/1998 | Orr | |
| 5,765,557 A | 6/1998 | Warters | |
| 5,795,322 A | 8/1998 | Boudewijn | |
| 5,800,455 A | 9/1998 | Palermo et al. | |
| 5,893,841 A | 4/1999 | Glickman | |
| 5,897,528 A | 4/1999 | Schultz | |
| 5,915,383 A | 6/1999 | Pagan | |
| 5,972,026 A | 10/1999 | Laufer et al. | |
| 6,083,255 A | 7/2000 | Laufer et al. | |
| 6,099,546 A | 8/2000 | Gia | |
| 6,174,307 B1 | 1/2001 | Daniel et al. | |
| 6,174,323 B1 | 1/2001 | Biggs et al. | |
| RE37,117 E | 3/2001 | Palermo | |
| 6,258,100 B1 | 7/2001 | Alferness et al. | |
| 6,287,290 B1 * | 9/2001 | Perkins et al. ................. 604/516 |
| 6,293,951 B1 * | 9/2001 | Alferness et al. ............ 606/108 |
| 6,398,775 B1 | 6/2002 | Perkins et al. | |
| 6,527,761 B1 | 3/2003 | Soltesz et al. | |
| 6,585,639 B1 | 7/2003 | Kotmel et al. | |
| 6,609,521 B1 | 8/2003 | Belani et al. | |
| 6,629,951 B2 | 10/2003 | Laufer et al. | |
| 6,679,264 B1 | 1/2004 | Deem et al. | |
| 6,692,494 B1 | 2/2004 | Cooper et al. | |
| 6,709,401 B2 | 3/2004 | Perkins et al. | |
| 6,712,812 B2 | 3/2004 | Roschak et al. | |
| 6,722,360 B2 | 4/2004 | Doshi | |
| 6,749,606 B2 | 6/2004 | Keast et al. | |
| 6,792,947 B1 | 9/2004 | Bowden | |
| 6,878,141 B1 | 4/2005 | Perkins et al. | |
| 6,886,558 B2 | 5/2005 | Tanaka | |
| 6,941,950 B2 | 9/2005 | Wilson et al. | |
| 6,997,189 B2 | 2/2006 | Biggs et al. | |
| 6,997,918 B2 | 2/2006 | Soltesz et al. | |
| 7,011,094 B2 | 3/2006 | Rapacki et al. | |
| 7,022,088 B2 | 4/2006 | Keast et al. | |
| 7,086,398 B2 | 8/2006 | Tanaka | |
| 7,276,077 B2 | 10/2007 | Zadno-Azizi et al. | |
| 7,449,010 B1 * | 11/2008 | Hayase et al. ............. 604/93.01 |
| 7,588,033 B2 | 9/2009 | Wondka | |
| 7,883,471 B2 | 2/2011 | Aljuri et al. | |
| 8,137,302 B2 | 3/2012 | Aljuri et al. | |
| 8,496,006 B2 * | 7/2013 | Aljuri et al. ............. 128/207.16 |
| 2001/0051899 A1 | 12/2001 | Kawashima et al. | |
| 2002/0049370 A1 | 4/2002 | Laufer et al. | |
| 2002/0062120 A1 | 5/2002 | Perkins et al. | |
| 2003/0051733 A1 | 3/2003 | Kotmel et al. | |
| 2003/0171332 A1 | 9/2003 | Abraham et al. | |
| 2003/0228344 A1 * | 12/2003 | Fields ....................... A61F 2/04 424/423 |
| 2004/0016435 A1 | 1/2004 | Deem et al. | |
| 2004/0243016 A1 | 12/2004 | Sanderson et al. | |
| 2005/0016530 A1 | 1/2005 | McCutcheon et al. | |

(56) References Cited

U.S. PATENT DOCUMENTS

| | | | |
|---|---|---|---|
| 2005/0022809 A1* | 2/2005 | Wondka | 128/200.24 |
| 2005/0126572 A1 | 6/2005 | Gosweiler | |
| 2005/0166924 A1 | 8/2005 | Thomas et al. | |
| 2005/0187561 A1 | 8/2005 | Lee-Sepsick et al. | |
| 2005/0288684 A1 | 12/2005 | Aronson et al. | |
| 2006/0095002 A1 | 5/2006 | Soltesz et al. | |
| 2006/0102186 A1 | 5/2006 | Adler | |
| 2006/0122647 A1 | 6/2006 | Callaghan et al. | |
| 2006/0129134 A1* | 6/2006 | Kerr | 604/539 |
| 2006/0264772 A1 | 11/2006 | Aljuri et al. | |
| 2006/0283462 A1 | 12/2006 | Fields et al. | |
| 2007/0005083 A1 | 1/2007 | Sabanathan et al. | |
| 2007/0096048 A1 | 5/2007 | Clerc | |
| 2007/0142742 A1 | 6/2007 | Aljuri et al. | |
| 2007/0225747 A1 | 9/2007 | Perkins et al. | |
| 2008/0051719 A1 | 2/2008 | Nair et al. | |
| 2008/0228130 A1 | 9/2008 | Aljuri et al. | |
| 2008/0228137 A1 | 9/2008 | Aljuri et al. | |
| 2009/0241964 A1* | 10/2009 | Aljuri et al. | 128/207.15 |
| 2009/0260625 A1 | 10/2009 | Wondka | |
| 2010/0031964 A1 | 2/2010 | Turek et al. | |
| 2011/0011406 A1 | 1/2011 | Blom et al. | |
| 2011/0152678 A1 | 6/2011 | Aljuri et al. | |
| 2011/0203594 A1 | 8/2011 | Brain | |
| 2011/0259339 A1 | 10/2011 | Isaza | |

FOREIGN PATENT DOCUMENTS

| | | |
|---|---|---|
| EP | 1078601 B1 | 10/2006 |
| JP | 2004-504867 A | 2/2004 |
| WO | WO 92/10971 A1 | 7/1992 |
| WO | WO 95/33506 A1 | 12/1995 |
| WO | WO 98/44854 A1 | 10/1998 |
| WO | WO 98/48706 A1 | 11/1998 |
| WO | WO 98/49191 A1 | 11/1998 |
| WO | WO 99/01076 A1 | 1/1999 |
| WO | WO 99/17827 A2 | 4/1999 |
| WO | WO 99/20332 A1 | 4/1999 |
| WO | WO 99/32040 A1 | 7/1999 |
| WO | WO 99/34741 A1 | 7/1999 |
| WO | WO 99/64109 A1 | 12/1999 |
| WO | WO 00/51510 A1 | 9/2000 |
| WO | WO 00/62699 A2 | 10/2000 |
| WO | WO 01/02042 A1 | 1/2001 |
| WO | WO 01/03642 A1 | 1/2001 |
| WO | WO 01/10314 A1 | 2/2001 |
| WO | WO 01/13839 A1 | 3/2001 |
| WO | WO 01/13908 A2 | 3/2001 |
| WO | WO 03/022124 A2 | 3/2003 |
| WO | WO 03/022221 A2 | 3/2003 |
| WO | WO 2006/055692 A2 | 5/2006 |
| WO | WO 2006/078451 A1 | 7/2006 |

OTHER PUBLICATIONS

Office action dated Nov. 1, 2013 for U.S. Appl. No. 12/407,709.
Office action dated Jul. 8, 2014 for U.S. Appl. No. 12/407,709.
U.S. Appl. No. 11/428,762, filed Jul. 5, 2006, Aljuri et al.
U.S. Appl. No. 60/828,496, filed Oct. 26, 2006, Nair et al.
Becker et al., "Lung Volumes Before and After Lung Volume Reduction Surgery," Am J Respir Crit Care Med, May 1998;157(5 Pt 1):1593-9.
Burger et al., "Gas exchange in the parabronchial lung of birds: Experiments in unidirectionally ventilated ducks," Respiration Physiology Mar. 1979; 36(1):19-37.
Criner et al., "Effect of Lung Volume Reduction Surgery on Diaphragm Strength," Am J Respir Crit Care Med, May 1998;157(5 Pt 1):1578-85.
European search report and opinion dated Nov. 16, 2009 for EP Application No. 06717427.6.
Harada et al., "Re-expansion of Refractory Atelectasis Using a Bronchofiberscope with a Balloon Cuff," Chest. Dec. 1983;84(6):725-8.
International search report and written opinion dated Aug. 26, 2008 for PCT/US2008/056706.
Kotloff et al., "Comparison of Short-term Functional Outcomes Following Unilateral and Bilateral Lung Volume Reduction Surgery," Chest. Apr. 1998;113(4):890-5.
Morrell et al., "Collateral ventilation and gas exchange during airway occlusion in the normal human lung," Am Rev Respir Dis. Mar. 1993;147(3):535-539.
Office action dated Apr. 11, 2012 for US Appl. No. 12/407,709.
Office action dated Apr. 15, 2010 for U.S. Appl. No. 11/685,008.
Office action dated Jul. 12, 2013 for U.S. Appl. No. 12/407,709.
Office action dated Aug. 1, 2012 for U.S. Appl. No. 12/820,547.
Office action dated Nov. 24, 2009 for U.S. Appl. No. 11/685,008.
Office action dated Dec. 17, 2012 for U.S. Appl. No. 12/407,709.
Ojo et al., "Lung Volume Reduction Surgery Alters Management of Pulmonary Nodules in Patients With Severe COPD," Chest. Dec. 1997;112(6):1494-500.
Sclafani, "Clearing the Airways," AARC Times, Jan. 1999, pp. 69-72.
Snell, et al. The potential for bronchoscopic lung volume reduction using bronchial prostheses. Chest. Sep. 2003; 124(3):1073-1080.
Woolcock et al., Mechanical Factors Influencing Collateral Ventilation in Human, Dog, and Pig Lungs, J Appl Physiol. Jan. 1971; 30(1):99-115.
Co-pending U.S. Appl. No. 14/703,670, filed May 4, 2015.
Notice of allowance dated Mar. 26, 2013 for U.S. Appl. No. 12/820,547.

* cited by examiner

METHODS AND DEVICES FOR PASSIVE RESIDUAL LUNG VOLUME REDUCTION AND FUNCTIONAL LUNG VOLUME EXPANSION

CROSS-REFERENCE TO RELATED APPLICATIONS

This application is a continuation of U.S. patent application Ser. No. 12/820,547, filed Jun. 22, 2010, which is a continuation-in-part of U.S. patent application Ser. No. 11/685,008, filed Mar. 12, 2007; U.S. patent application Ser. No. 12/820,547, is also a continuation-in-part of U.S. patent application Ser. No. 11/296,951, filed Dec. 7, 2005, now U.S. Pat. No. 7,883,471, which claims the benefit and priority of U.S. Provisional Patent Application Nos. 60/645,711, filed Jan. 20, 2005; 60/696,940, filed Jul. 5, 2005; and 60/699,289, filed Jul. 13, 2005. The full disclosures of all the above-referenced patent applications are hereby incorporated herein by reference.

BACKGROUND OF THE INVENTION

1. Field of the Invention

The present invention relates generally to medical methods and apparatus. More particularly, the present invention relates to methods and apparatus for endobronchial residual lung volume reduction by passive deflation of hyperinflated segments with functional lung volume expansion as a result.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none is completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air that goes into the lungs but is unable to transfer oxygen to the blood. Lung volume reduction is conventionally performed in open chest or thoracoscopic procedures where the lung is resected, typically using stapling devices having integral cutting blades.

While effective in many cases, conventional lung volume reduction surgery is significantly traumatic to the patient, even when thoracoscopic procedures are employed. Such procedures often result in the unintentional removal of healthy lung tissue and frequently leave perforations or other discontinuities in the lung, which result in air leakage from the remaining lung. Even technically successful procedures can cause respiratory failure, pneumonia, and death. In addition, many older or compromised patients are not able to be candidates for these procedures.

As an improvement over open surgical and minimally invasive lung volume reduction procedures, endobronchial lung volume reduction procedures have been proposed. For example, U.S. Pat. Nos. 6,258,100 and 6,679,264 describe placement of one-way valve structures in the airways leading to diseased lung regions. It is expected that the valve structures will allow air to be expelled from the diseased region of the lung while blocking reinflation of the diseased region. Thus, over time, the volume of the diseased region will be reduced and the patient condition will improve.

While promising, the use of implantable, one-way valve structures is problematic in at least several respects. The valves must be implanted prior to assessing whether they are functioning properly. Thus, if the valve fails to either allow expiratory flow from or inhibit inspiratory flow into the diseased region, that failure will only be determined after the valve structure has been implanted, requiring surgical removal. Additionally, even if the valve structure functions properly, many patients have diseased lung segments with collateral flow from adjacent, healthy lung segments. In those patients, the lung volume reduction of the diseased region will be significantly impaired, even after successfully occluding inspiration through the main airway leading to the diseased region, since air will enter collaterally from the adjacent healthy lung region. When implanting one-way valve structures, the existence of such collateral flow will only be evident after the lung region fails to deflate over time, requiring further treatment.

For these reasons, it would be desirable to provide improved and alternative methods and apparatus for effecting residual lung volume reduction in hyperinflated and other diseased lung regions. The methods and apparatus will preferably allow for passive deflation of an isolated lung region without the need to implant a one-way valve structure in the lung. The methods and apparatus will preferably be compatible with known protocols for occluding diseased lung segments and regions after deflation, such as placement of plugs and occluding members within the airways leading to such diseased segments and regions. Additionally, such methods and devices should be compatible with protocols for identifying and treating patients having diseased lung segments and regions which suffer from collateral flow with adjacent healthy lung regions. At least some of these objectives will be met by the inventions described hereinbelow.

2. Description of the Background Art

Methods for performing minimally invasive and endobronchial lung volume reduction are described in the following patents and publications: U.S. Pat. Nos. 5,972,026; 6,083,255; 6,258,100; 6,287,290; 6,398,775; 6,527,761; 6,585,639; 6,679,264; 6,709,401; 6,878,141; 6,997,918; 2001/0051899; and 2004/0016435.

BRIEF SUMMARY OF THE INVENTION

The present invention provides methods and apparatus for passively reducing the residual volume (the volume of air remaining after maximal exhalation) of a hyperinflated or otherwise diseased lung compartment or segment. By "passively reducing," it is meant that air can be removed from the diseased lung region without the use of a vacuum aspiration to draw the air from the region. Typically, such passive reduction will rely on a non-implanted one-way flow structure, which permits air to be exhaled or exhausted from the lung region while preventing or inhibiting the inspiration of air back into the lung region. Thus, the methods of the present invention will not require the permanent implantation of valves or other structures prior to actually achieving the desired residual lung volume reduction, as with the one-way implantable valve structures of the prior art.

The methods and apparatus of the present invention can be terminated and all apparatus removed should it appear for any reason that the desired residual lung volume reduction is not being achieved. Commonly, such failure can be the result of collateral flow into the diseased lung region from adjacent healthy lung region(s). In such cases, steps can be taken to limit or stop the collateral flow and allow resumption of the passive lung volume reduction protocols. In other cases, it might be desirable or necessary to employ open surgical, thoracoscopic, or other surgical procedures for lung resection.

Patients who successfully achieve residual volume reduction of hyperinflated or other diseased lung regions in accordance with the principles of the present invention will typically have those regions sealed permanently to prevent reinflation. Such sealing can be achieved by a variety of known techniques, including the application of radiofrequency or other energy for shrinking or sealing the walls of the airways feeding the lung region. Alternatively, synthetic or biological glues could be used for achieving sealing of the airway walls. Most commonly, however, expandable plugs will be implanted in the airways leading to the deflated lung region to achieve the sealing.

In a first aspect of the present invention, methods for reducing the residual volume of a hyperinflated lung compartment comprise sealingly engaging a distal end of a catheter in an airway feeding the lung compartment. Air is allowed to be expelled from the lung compartment through a passage in the catheter while the patient is exhaling, and air is blocked from re-entering the lung compartment through the catheter passage while the patient is inhaling. As the residual volume diminishes, the hyperinflated lung compartment reduces in size freeing up the previously occupied space in the thoracic cavity. Consequently, a greater fraction of the Total Lung Capacity (TLC), which is the volumetric space contained in the thoracic cavity that is occupied by lung tissue after a full inhalation, becomes available for the healthier lung compartments to expand, and the volume of the lung available for gas exchange commonly referred to in clinical practice as the lung's Functional Vital Capacity (FVC) or Vital Capacity (VC) increases, the result of which is effectively a functional lung volume expansion.

The hyperinflated lung compartment will usually be substantially free of collateral flow from adjacent lung compartments, and optionally the patient can be tested for the presence of such collateral flow, for example using techniques taught in copending, commonly assigned application Ser. No. 11/296,951, filed on Dec. 7, 2005; Ser. No. 11/550, 660, filed on Oct. 18, 2006; and application Ser. No. 11/428,762, filed on Jul. 5, 2006, the full disclosures of which are incorporated herein by reference.

Figure 7:
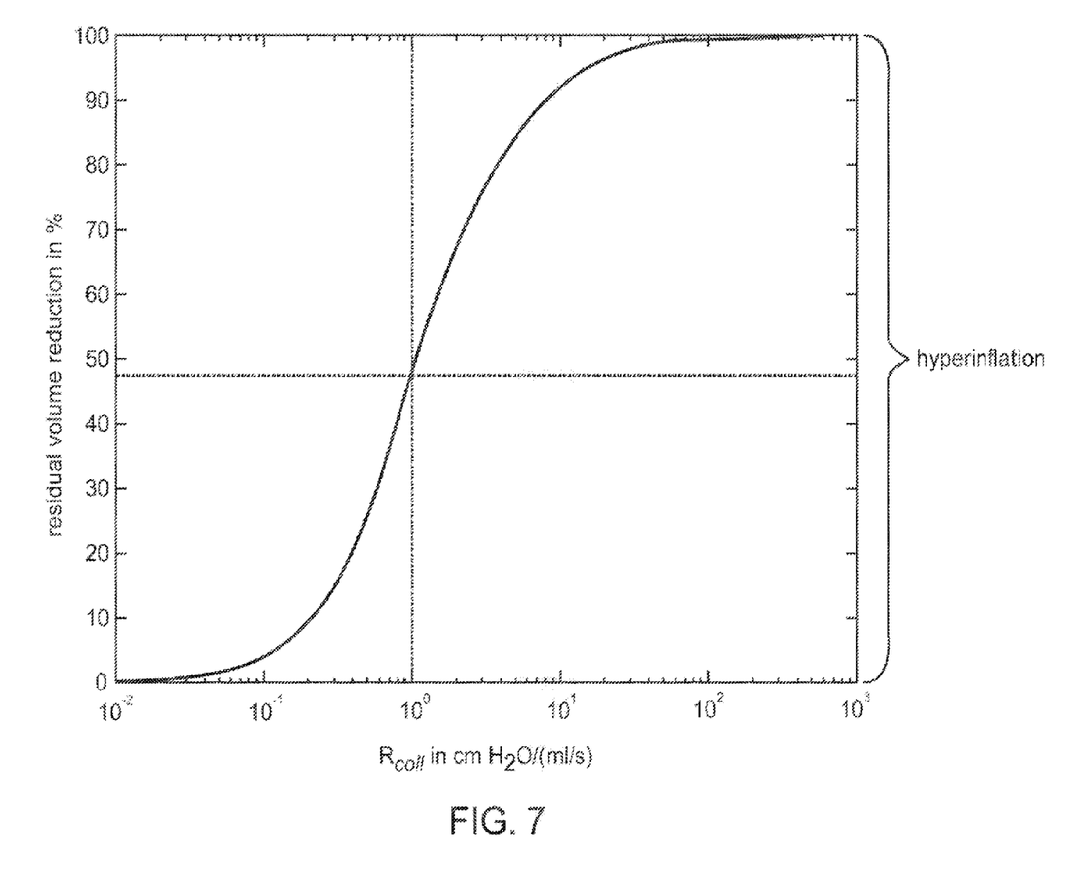
FIG. 7 is a graph showing the relationship between collateral resistance R.sub.coll and residual volume reduction in an isolated lung compartment.

Alternatively, the methods of the present invention for reducing residual lung volume can be performed in patients having collateral flow channels leading into the hyperinflated or other diseased lung compartment. In such cases, the collateral flow channels may first be blocked, for example, by introducing glues, occlusive particles, hydrogels or other blocking substances, as taught for example in copending application Ser. No. 11/684,950, filed on Mar. 12, 2007, the full disclosure of which is incorporated herein by reference. In other cases, where the flow channels are relatively small, those channels will partially or fully collapse as the residual lung volume is reduced. In such cases, the patient may be treated as if the collateral flow channels did not exist. The effectiveness of reduction in hyperinflation, however, will depend on the collateral resistance between the hyperinflated compartment and the neighboring compartments, as illustrated in FIG. 7, where residual volume reduction is negligible when the resistance to collateral flow R.sub.coll is very small (significant collateral flow channels) and maximally effective when R.sub.coll is very high (no collateral flow channels).

In all of the above methods, it may be desirable to introduce an oxygen-rich gas into the lung compartment while or after the lung volume is reduced in order to induce or promote absorption atelectasis. Absorption atelectasis promotes absorption of the remaining or residual gas in the compartment into the blood to further reduce the volume, either before or after permanent sealing of the lung volume compartment or segment.

In a second aspect, the present invention provides catheters for isolating and deflating hyperinflated and other diseased lung compartments. The catheter comprises a catheter body, an expandable occluding member on the catheter body, and a one-way flow element associated with the catheter body. The catheter body usually has a distal end, a proximal end, and at least one lumen extending from a location at or near the distal end to a location at or near the proximal end. At least a distal portion of the catheter body is adapted to be advanced into and through the airways of a lung so that the distal end can reach an airway that feeds a target lung compartment or segment to be treated. The expandable occluding member is disposed near the distal end of the catheter body and is adapted to be expanded in the airway that feeds the target lung compartment or segment so that said compartment or segment can be isolated, with access provided only through the lumen or catheter body when the occluding member is expanded. The one-way flow element is adapted to be disposed within or in-line with the lumen of the catheter body in order to allow flow in a distal-to-proximal direction so that air will be expelled from the isolated lung compartment or segment as the patient exhales. The one-way flow element, however, inhibits or prevents flow through the lumen in a proximal-to-distal direction so that air cannot enter the isolated lung compartment or segment while the patient is inhaling.

For the intended endobronchial deployment, the catheter body will typically have a length in the range from 20 cm to 200 cm, preferably from 80 cm to 120 cm, and a diameter near the distal end in the range from 0.1 mm to 10 mm, preferably from 1 mm to 5 mm. The expandable occluding member will typically be an inflatable balloon or cuff, where the balloon or cuff has a width in the range from 1 mm to 30 mm, preferably from 5 mm to 20 mm, when inflated. The one-way flow element is typically a conventional one-way flow valve, such as a duck-bill valve, a flap valve, or the like, which is disposed in the lumen of the catheter body, either near the distal end or at any other point within the lumen. Alternatively, the one-way flow element could be provided as a separate component, for example provided in a hub which is detachably mounted at the proximal end of the catheter body. In other instances, it might be desirable to provide two or more one-way flow elements in series within the lumen or otherwise provided in-line with the lumen in order to enhance sealing in the inspiratory direction through the lumen.

In a third aspect of the present invention, a method for determining whether collateral ventilation of a hyperinflated lung compartment is present may involve: sealing a distal end of a catheter in an airway feeding the lung compartment; allowing air to be expelled from the lung compartment through a passage in the catheter while the patient is exhaling; blocking air from entering the lung compartment through the catheter passage while the patient is inhaling; comparing an image of the lung compartment with an earlier image of the lung compartment acquired before the sealing step; and determining whether collateral ventilation is present in the lung compartment, based on comparing the image and the earlier image. In one embodiment, the compared images are CT scans, although in other embodiments alternative imaging modalities may be used, such as MRI, conventional radiographs and/or the like. Typically, though not necessarily, the before and after images will be compared based on size, with a smaller size after catheter placement indicating a lack of significant collateral ventilation and little or no change in size indicating likely significant collateral ventilation.

Optionally, one embodiment may involve advancing the catheter through a bronchoscope to position the catheter distal end in the airway before sealing. In one such embodiment, the method may also involve: detaching a hub from a proximal end of the catheter; removing the bronchoscope from the airway by sliding it proximally over the catheter, thus leaving the catheter in the airway; and acquiring the image of the lung compartment. The catheter may be left in the airway for any suitable amount of time before acquiring the image—for example in one embodiment between about five minutes and about twenty-four hours. In some embodiments, where it is determined that there is minimal or no significant collateral ventilation of the lung compartment, the method may further include treating the airway to permanently limit airflow into the lung compartment.

These and other aspects and embodiments are described in further detail below, with reference to the attached drawing figures.

DETAILED DESCRIPTION OF THE INVENTION

Figure 1:
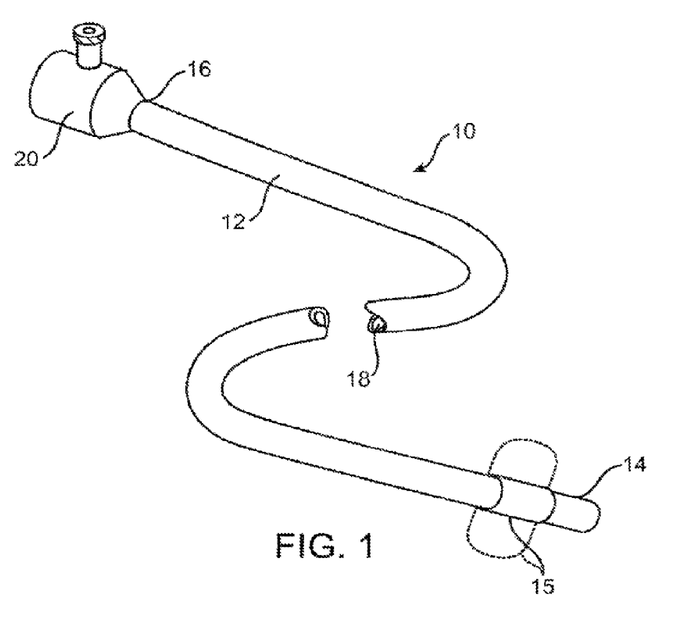
FIG. 1 is a perspective view of an isolation and deflation catheter constructed in accordance with the principles of the present invention.

Referring to FIG. 1, an endobronchial lung volume reduction catheter 10 constructed in accordance with the principles of the present invention includes an elongate catheter body 12 having a distal end 14, a proximal end 16, and an expandable occluding member 15, such as an inflatable balloon, mounted near the distal end 14. Catheter body 12 also includes at least one lumen or central passage 18 extending generally from the distal end 14 to the proximal end 16. Lumen 18 has a distal opening 19 at or near the distal end 14 in order to permit air or other lung gases to enter the lumen 18 and flow in a distal-to-proximal direction out through the proximal end of the lumen 18. Optionally, a hub 20 will be provided at the proximal end 16, but the hub 20 is not a necessary component of the catheter 10.

The catheter 10 is equipped to seal the area between the catheter body 12 and the bronchial wall such that only the lumen 18 is communicating with the airways distal to the seal. The seal, or isolation, is accomplished by the use of the occluding member 15, such as an inflatable member, attached to (or near) the distal tip 14 of the catheter 10. When there is an absence of collateral channels connecting the targeted isolated compartment to the rest of the lung, the isolated compartment will unsuccessfully attempt to draw air from the catheter lumen 18 during inspiration of normal respiration of the patient. Hence, during exhalation no air is returned to the catheter lumen. In the presence of collateral channels, an additional amount of air is available to the isolated compartment during the inspiratory phase of each breath, namely the air traveling from the neighboring compartment(s) through the collateral channels, which enables volumetric expansion of the isolated compartment during inspiration, resulting during expiration in air movement away from the isolated compartment to atmosphere through the catheter lumen and the collateral channels. If it is desired to perform Endobronchial Volume Reduction (EVR) on a lung compartment, the lung compartment may be analyzed for collateral ventilation prior to treatment to determine the likelihood of success of such treatment. Further, if undesired levels of collateral ventilation are measured, the collateral ventilation may be reduced to a desired level prior to treatment to ensure success of such treatment.

Figure 2:
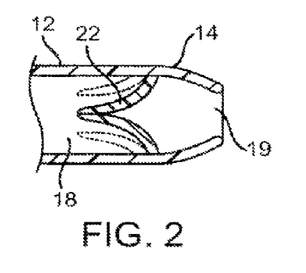
FIGS. 2-4 illustrate alternative placements of one-way flow elements within a central lumen of the catheter of FIG. 1.
Figure 3:
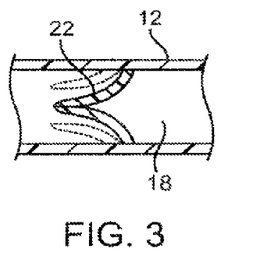

The present invention relies on placement of a one-way flow element within or in-line with the lumen 18 so that flow from an isolated lung compartment or segment (as described hereinbelow) may occur in a distal-to-proximal direction but flow back into the lung compartment or segment is inhibited or blocked in the proximal-to-distal direction. As shown in FIG. 2, in one embodiment a one-way flow element 22 may be provided in the lumen 18 near the distal end 14 of the catheter body 12, immediately proximal of the distal opening 19. In an alternative embodiment, as in FIG. 3, the same one-way flow element 22 may be provided in the lumen 18 more proximally (either still near the distal end 14 or even more proximally in some embodiments). As shown in FIGS. 2 and 3, the one-way flow element 22 may be a duck-bill valve, which opens as shown in broken line as the patient exhales to increase the pressure on the upstream or distal side of the valve 22. As the patient inhales, the pressure on the upstream or distal side of the valve is reduced, drawing the valve leaflets closed as shown in solid line.

Alternatively or additionally, the one-way flow element 22 could be provided anywhere else in the lumen 18, and two, three, four, or more such valve structures could be included in order to provide redundancy. In some embodiments where the one-way flow element 22 (or elements) is located within the lumen 18 of the catheter body 12, the hub 20 may be removable, or alternatively the catheter 10 may not include a hub. As will be explained further below, this may facilitate leaving the catheter 10 in a patient for diagnostic and/or treatment purposes. For example, if the catheter 10 is advanced into a patient through a bronchoscope, the hub 20 may be detached to allow the bronchoscope to be removed proximally over the catheter 10, thus leaving the catheter body 12 with the one-way flow element 22 in the patient.

Figure 4:
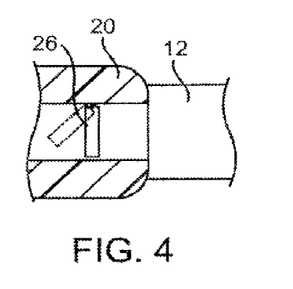

As a third option, a one-way valve structure 26 in the form of a flap valve could be provided within the hub 20. The hub 20 could be removable or permanently fixed to the catheter body 12. Other structures for providing in-line flow control could also be utilized.

In some embodiments, the catheter 10 may be coupled with a one-way valve, a flow-measuring device or/and a pressure sensor, all of which are external to the body of the patient and are placed in series so as to communicate with the catheter's inside lumen 18. The one-way valve prevents air from entering the target lung compartment from atmosphere but allows free air movement from the target lung compartment to atmosphere. The flow measuring device, the pressure sensor device and the one-way valve can be placed anywhere along the length of the catheter lumen 18. The seal provided by the catheter 10 results, during expiration, in air movement away from the isolated lung compartment to atmosphere through the catheter lumen 18 and the collateral channels. Thus, air is expelled through the catheter lumen 18 during each exhalation and will register as positive airflow on the flow-measuring device. Depending on the system dynamics, some air may be expelled through the catheter lumen 18 during exhalation in the absence of collateral channels, however at a different rate, volume and trend than that in the presence of collateral channels.

Figure 5:
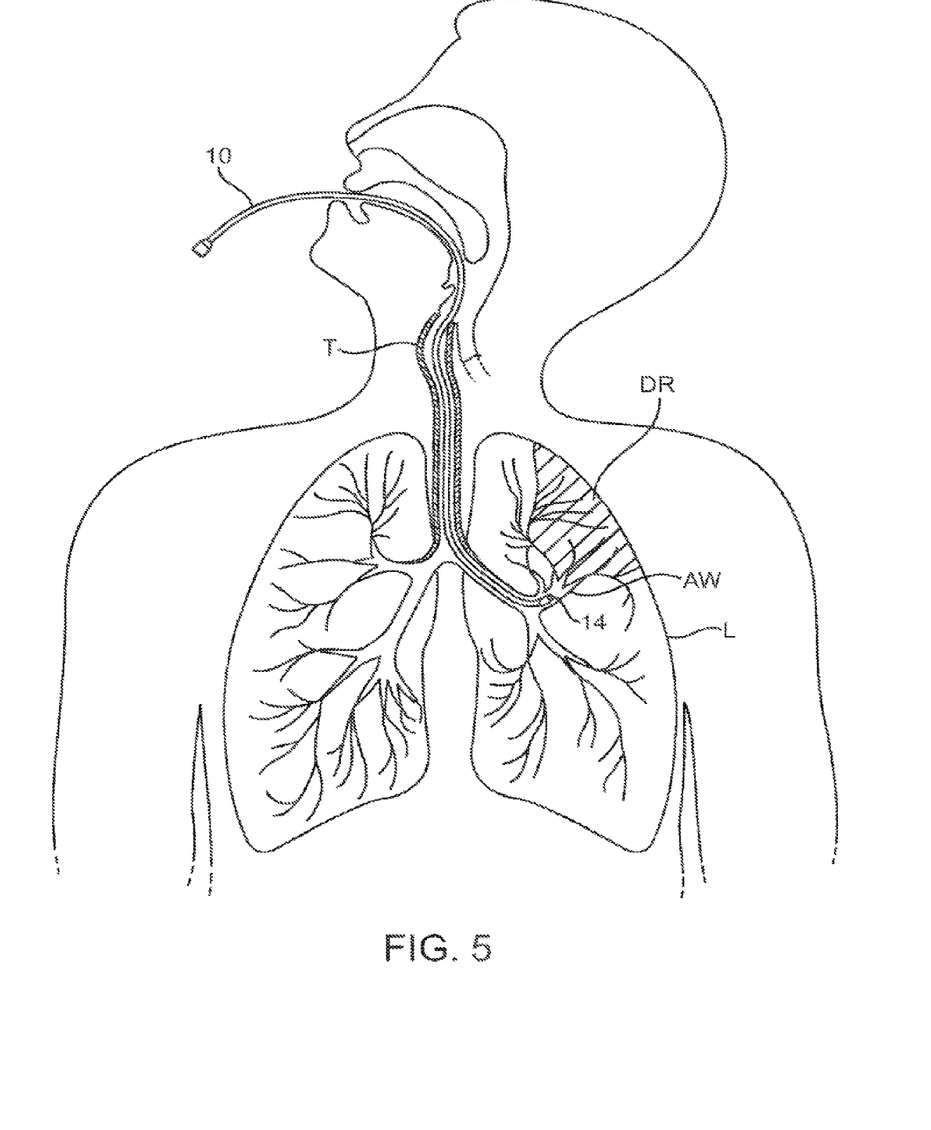
FIG. 5 illustrates the trans-tracheal endobronchial placement of the catheter of FIG. 1 in an airway leading to a diseased lung region in accordance with the principles of the present invention.

Use of the endobronchial lung volume reduction catheter 10 to reduce the residual volume of a diseased region DR of a lung L is illustrated beginning in FIG. 5. Catheter 10 is introduced through the patient's mouth, down past the trachea T and into a lung L. The distal end 14 of the catheter 10 is advanced to the main airway AW leading into the diseased region DR of the lung. Introduction and guidance of the catheter 10 may be achieved in conventional manners, such as described in commonly-owned U.S. Pat. Nos. 6,287, 290; 6,398,775; and 6,527,761, the full disclosures of which are incorporated herein by reference. In some embodiments, the catheter may be introduced through a flexible bronchoscope (not shown in FIG. 5).

Figure 6A:
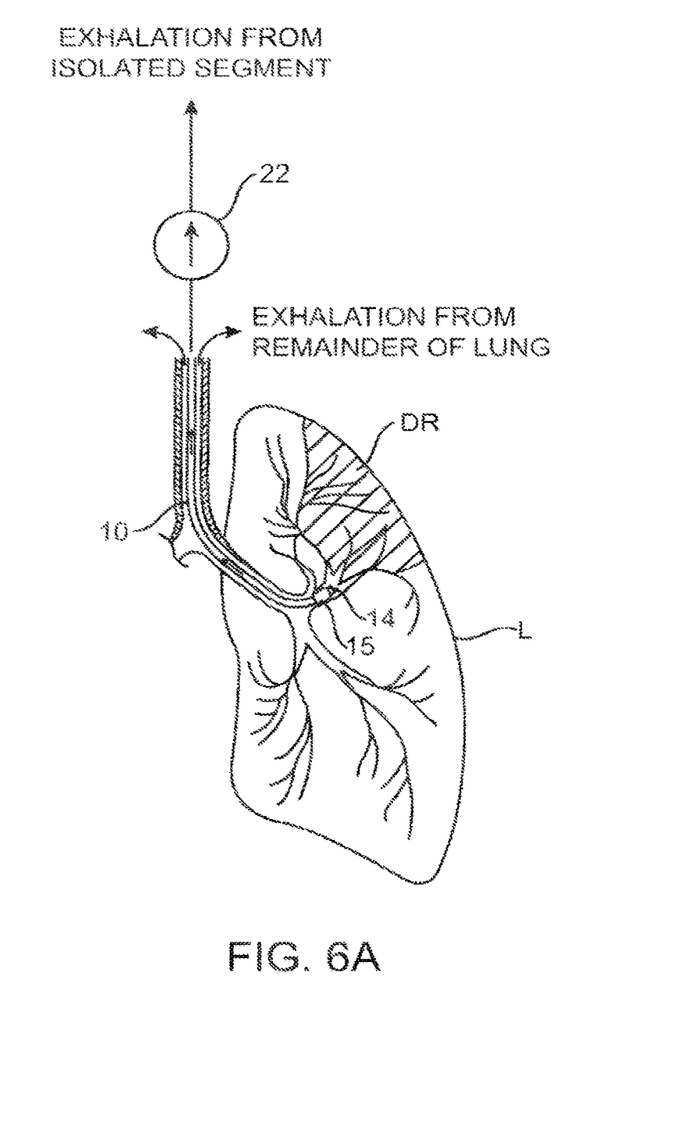
FIGS. 6A-6D illustrate use of the catheter as placed in FIG. 5 for isolating and reduction of the volume of the diseased lung region in accordance with the principles of the present invention.

Referring now to FIGS. 6A-6D, functioning of the one-way valve element in achieving the desired lung volume reduction will be described. After the distal end 14 of the catheter 10 is advanced to the feeding airway AW, the expandable occluding element 15 is expanded to occlude the airway. The expandable occluding element may be a balloon, cuff, or a braided balloon as described in copending application Ser. Nos. 60/823,734, filed on Aug. 28, 2006, and 60/828,496 filed on Oct. 6, 2006, the full disclosures of which are incorporated herein by reference. At that point, the only path between the atmosphere and the diseased region DR of the lung is through the lumen 18 of the catheter 10. As the patient exhales, as shown in FIG. 6A, air from the diseased region DR flows outwardly through the lumen 18 and the one-way valve element 22, causing a reduction in residual air within the region and a consequent reduction in volume. Air from the remainder of the lung also passes outward in the annular region around the catheter 10 in a normal manner.

Figure 6B:
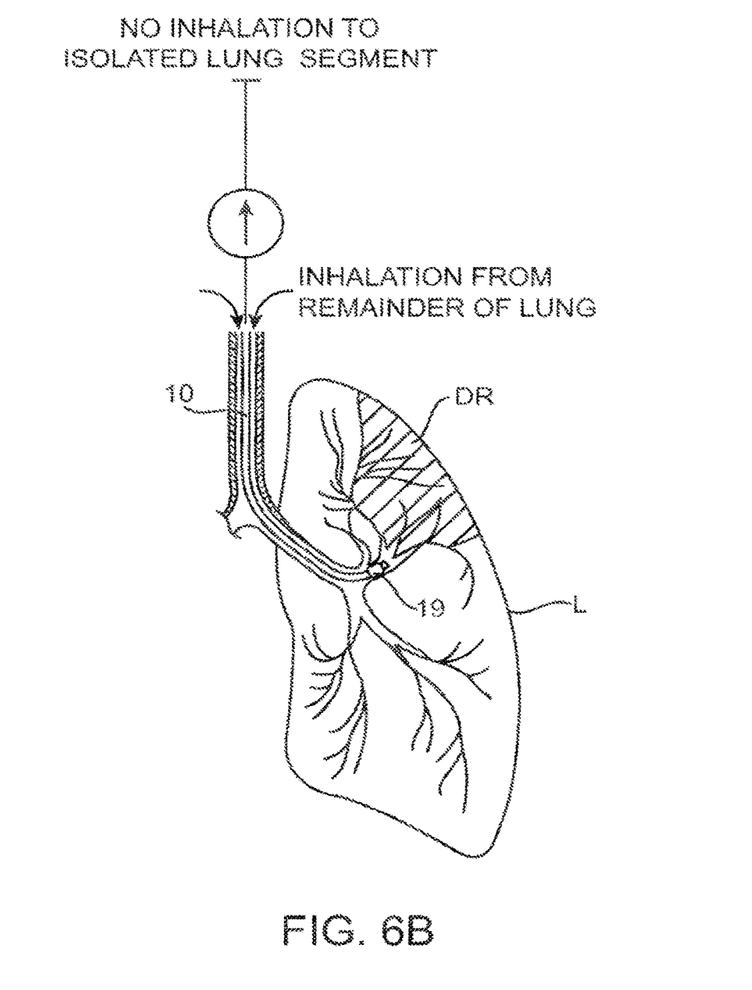

As shown in FIG. 6B, in contrast, when the patient inhales, no air enters the diseased regions DR of the lung L (as long as there are no significant collateral passageways), while the remainder of the lung is ventilated through the region around the catheter. As the patient continues to inhale and exhale, the air in the diseased region DR is incrementally exhausted, further reducing the lung volume as the external pressure from the surrounding regions of the lung is increased relative to the pressure within the diseased region.

Figure 6C:
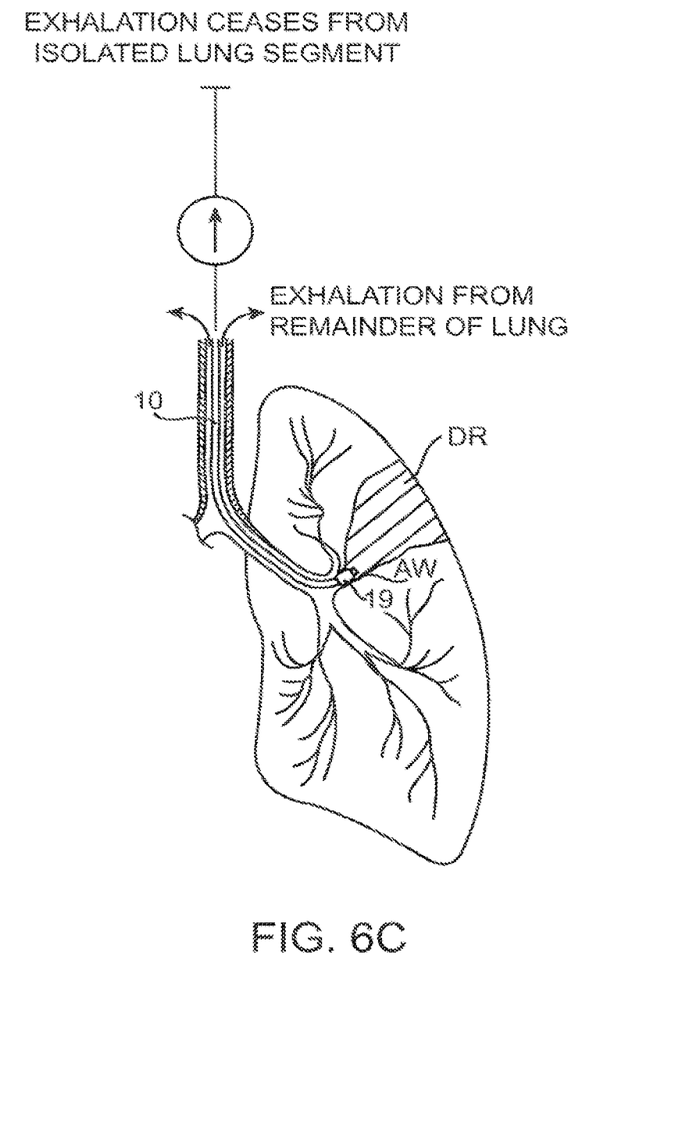
Figure 6D:
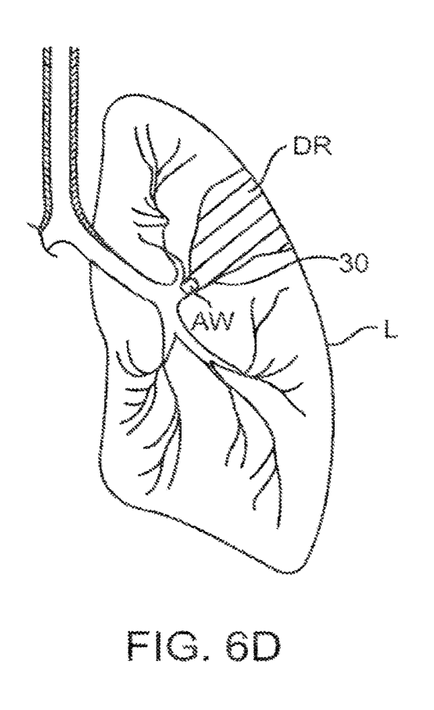

As shown in FIG. 6C, after some time, typically seconds to minutes, air flow from the isolated lung segment will stop and a maximum or near-maximum level of residual lung volume reduction within the diseased region DR will have been achieved. At that time, treating the patient may comprise occluding the airway AW feeding the diseased region DR, by applying heat, radiofrequency energy, glues, or preferably by implanting an occluding element 30, as shown in FIG. 6D. Implantation of the occluding element may be achieved by any of the techniques described in commonly-owned U.S. Pat. Nos. 6,287,290; and 6,527,761, the full disclosures of which have been previously incorporated herein by reference. In some embodiments, before more permanently occluding the airway, treating the patient may comprise aspirating the target lung compartment. When accessing a lung compartment through an occlusal stent, volume reduction therapy may be performed by aspirating through the catheter and stent. The catheter is then removed and the volume reduction maintained.

As described in greater detail in U.S. patent application Ser. No. 11/296,951, from which the present application claims priority and which has been previously incorporated by reference, a catheter 10 as described herein may also be used to determine whether collateral ventilation is present in a lung. The '951 application describes a number of methods and devices for use in determining such collateral ventilation. Additionally or alternatively to those methods/devices, in one embodiment a catheter 10 (as described above) may be advanced through a bronchoscope and deployed as described in relation to FIGS. 5 and 6A-6D of the present application. In this embodiment, the catheter 10 includes at least one one-way flow element 22 within the lumen 18 of the catheter body 12. The hub 20 of the catheter 10 may then be detached, and the bronchoscope may be removed proximally over the catheter body 12, leaving the catheter body 12 in place in the patient. After a desired amount of time (anywhere from several minutes to twenty-four hours or more), an imaging study such as a CT scan may be taken of the patient's lung to see if the residual volume of the diseased lung compartment has decreased. Typically, this CT scan or other imaging study will be compared to a similar study taken before placement of the catheter 10 to determine if placement of the catheter has caused a reduction in residual volume in the lung compartment. If a reduction is noted, this may indicate that collateral ventilation is absent or minimal. This type of assessment may be used to help decide whether to treat a lung compartment further, such as with an implantable valve or blocking element.

In an alternative embodiment, the hub 20 of the catheter 10 may be left on, and the catheter 10 and bronchoscope may be left in the patient for a short time while an imaging study is performed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for reducing the residual volume of a hyperinflated lung compartment, said method comprising:
    sealing a distal end of a catheter in an airway feeding the lung compartment by using an occluding member that is adapted to be expanded in an airway which feeds the hyperinflated lung compartment such that access to the compartment is provided only through a passage of the catheter when the occluding member is expanded;
    allowing air to be expelled from the lung compartment through a passage in the catheter while the patient is exhaling;
    blocking air from entering the lung compartment through the catheter passage while the patient is inhaling by using a one-way flow element adapted to be disposed within or in-line with the passage of the catheter so that flow in a distal-to-proximal direction is allowed and flow in a proximal-to-distal direction is inhibited or prevented;

determining whether collateral flow channels with one or more adjacent lung compartments are present in the lung compartment;

determining whether collateral ventilation is present in the lung compartment, and wherein determining whether collateral ventilation is present comprises:

detecting, using a flow-measuring device, air flow or accumulation from the isolated lung compartment over time; and calculating, using a computer, a value of collateral resistance; and diagnosing collateral ventilation between the target lung compartment and at least one adjacent lung compartment based on the value of collateral resistance calculated by the computer; and treating the collateral flow channels by blocking said channels.

2. A method as in claim 1, further comprising introducing an oxygen-rich gas into the lung compartment after the volume is reduced to induce or promote absorption atelectasis.

3. A method as in claim 1, further comprising by introducing glues to block the collateral flow channels.

4. A method as in claim 1, further comprising by introducing occlusive particles to block the collateral flow channels.

5. A method as in claim 1, further comprising by introducing hydrogels to block the collateral flow channels.

\* \* \* \* \*